United States Patent
Enzien et al.

(10) Patent No.: US 9,469,860 B2
(45) Date of Patent: Oct. 18, 2016

(54) METHOD FOR PRODUCTION OF N-BUTANOL FROM SYNGAS USING SYNTROPHIC CO-CULTURES OF ANAEROBIC MICROORGANISMS

(71) Applicant: Coskata, Inc., Warrenville, IL (US)

(72) Inventors: Mike Enzien, Lisle, IL (US); Rathin Datta, Chicago, IL (US); Richard Tobey, St. Charles, IL (US)

(73) Assignee: SYNATA BIO, INC., Warrenville, IL (US)

( * ) Notice: Subject to any disclaimer, the term of this patent is extended or adjusted under 35 U.S.C. 154(b) by 0 days.

(21) Appl. No.: 13/745,155

(22) Filed: Jan. 18, 2013

(65) Prior Publication Data

US 2014/0206052 A1 Jul. 24, 2014

(51) Int. Cl.
*C12P 7/16* (2006.01)
*C12P 7/06* (2006.01)
*C12P 7/54* (2006.01)

(52) U.S. Cl.
CPC .. C12P 7/16 (2013.01); *C12P 7/06* (2013.01); *C12P 7/54* (2013.01); *Y02E 50/10* (2013.01); *Y02T 50/678* (2013.01)

(58) Field of Classification Search
None
See application file for complete search history.

(56) References Cited

U.S. PATENT DOCUMENTS

| | | | |
|---|---|---|---|
| 4,539,293 A * | 9/1985 | Bergstrom et al. | 435/160 |
| 5,753,474 A * | 5/1998 | Ramey | 435/136 |
| 7,285,402 B2 * | 10/2007 | Gaddy et al. | 435/161 |
| 7,704,723 B2 * | 4/2010 | Huhnke et al. | 435/252.1 |
| 7,851,188 B2 | 12/2010 | Donaldson et al. | |
| 7,972,824 B2 * | 7/2011 | Simpson et al. | 435/155 |
| 8,017,375 B2 | 9/2011 | Feldman et al. | |
| 8,048,661 B2 | 11/2011 | Burgard et al. | |
| 8,129,155 B2 * | 3/2012 | Trawick et al. | 435/146 |
| 8,445,244 B2 | 5/2013 | Burgard et al. | |
| 8,551,746 B2 | 10/2013 | Reeves et al. | |
| 2007/0275447 A1 * | 11/2007 | Lewis et al. | 435/161 |
| 2009/0029434 A1 | 1/2009 | Tsai et al. | |
| 2009/0155869 A1 | 6/2009 | Buelter et al. | |
| 2009/0215142 A1 | 8/2009 | Tsai et al. | |
| 2009/0215153 A1 | 8/2009 | Tsai et al. | |
| 2010/0047886 A1 | 2/2010 | Hickey et al. | |
| 2010/0120106 A1 * | 5/2010 | Kohn et al. | 435/160 |
| 2010/0136640 A1 | 6/2010 | Lee et al. | |
| 2010/0151543 A1 | 6/2010 | Reeves | |
| 2010/0285548 A1 * | 11/2010 | Friedmann et al. | 435/158 |
| 2010/0323418 A1 * | 12/2010 | Burgard | 435/160 |
| 2011/0008858 A1 * | 1/2011 | Osterhout et al. | 435/148 |

(Continued)

FOREIGN PATENT DOCUMENTS

WO WO2012003373 A2 * 1/2012
WO WO2012136826 A1 10/2012

OTHER PUBLICATIONS

Beesch, S.C., A Microbiological process Report—Applied Microbiology, 1: 85-95 (1953).

(Continued)

*Primary Examiner* — Robert Mondesi
*Assistant Examiner* — Richard Ekstrom
(74) *Attorney, Agent, or Firm* — McDonnell Boehnen Hulbert & Berghoff LLP (57) ABSTRACT

This invention provides methods and systems for the production of butanol. Specifically, the methods and systems of the present invention use syntrophic co-cultures for the production of butanol from syngas.

12 Claims, 5 Drawing Sheets

(56) References Cited

U.S. PATENT DOCUMENTS

| | | | | |
|---|---|---|---|---|
| 2011/0008860 | A1* | 1/2011 | Reeves et al. | 435/161 |
| 2011/0104770 | A1* | 5/2011 | Tobey | 435/140 |
| 2011/0117615 | A1* | 5/2011 | Green et al. | 435/136 |
| 2011/0236941 | A1* | 9/2011 | Koepke et al. | 435/160 |
| 2011/0256597 | A1* | 10/2011 | Hickey et al. | 435/140 |
| 2012/0034664 | A1* | 2/2012 | Kohn et al. | 435/140 |

OTHER PUBLICATIONS

Marlatt, et al., Acetone-Butanol Fermentation Process Developmental and Economic Evaluation, Biotechnology Progress, 2(1):23-28 (1986).

Green et al., Genetic manipulation of acid formation pathways by gene inactivation in Clostridium acetobutylicum ATCC 824, Microbiology,142: 2079-2086 (1996).

X. Liu et al., Construction and Characterization of ack Deleted Mutant of Clostridium tyrobutyricum for Enhanced Butyric Acid and Hydrogen Production, Biotechnology Prog., 22: 1265-1275 (2006).

A. Grethlein et al., Evidence of n-Butanol Production from Carbon Monoxide by Butyribacterium methylotrophicum, Journal of Fermentation and Bioengineering, 72(1): 58-60 (1991).

Grethlien et al., Continuous Production of Mixed Alcohols and Acids from Carbon Monoxide, Applied Biochemistry and Biotechnology, 24-25(1):875-885 (1990).

Liou et al., *Clostridium carboxidivorans* sp. nov. a solvent producing clostridium isolated from an agricultural settling lagoon, and reclassification of the acetogen Clostridium scatolgenes strain SL1 as *Clostridium drakei* sp. nov., Internation Journal of Systematic and Evolutionary Microbiology 55(5):2085-2091 (2005).

Worden et al., Production of butanol and ethanol from synthesis gas via fermentation, Fuel, 70: 615-619 (1991).

M. Bredwell et al., Reactor design issues for synthesis-gas fermentations, Biotechnology Progress 15: 834-844 (1999).

Klasson et al., Biological conversion of synthesis gas into fuels, International Journal of Hydrogen Energy 17 (4):281-288 (1992).

J. Vega et al., The Biological Production of Ethanol from Synthesis Gas, Applied Biochemistry and Biotechnology, 20-1:781-796 (1989).

J. Abrini,et al., "*Clostridium autoethanogenum*, Sp-Nov, an Anaerobic Bacterium That Produces Ethanol from Carbon-Monoxide", Archives of Microbiology, 161(4):345-351 (1994).

Balch, et al., New Approach to the Cultivation of Methanogenic Bacteria: 2-Mercaptoethanesulfonic Acid (HS-CoM)-Dependent Growth of Methanobacterium ruminantium in a Pressurized Atmosphere, Appl. Environ. Microbiol. 32 (6):781-791 (1976).

Balch et al., Methanogens: Reevaluation of a Unique Biological Gropu, Microbiol. Rev. 43(2):260-296 (1979).

Bruant et al., Genomic Analysis of Carbon Monoxide Utilization and Butanol Production by Clostridium carboxidivorans, PLoS One, 5(9) e13033 (2010).

Abbas, A., The synergistic effects of probiotic microorganisms on the microbial production of butyrate in vitro, Mcnair Scholars Research Journal, 2(1):103-113 (2009).

Duncan, et al., Acetate utilization and butyryl coenzyme a (CoA): acetate-CoA transferase in Butyrate-producing bacteria from the human large intestine, Applied and Environmental Microbiology, 68(10):5186-5190 (2002).

International Search Report and Written Opinion for International application No. PCT/US2013/078362 mailed on Apr. 23, 2014.

International Search Report and Written Opinion for International Application No. PCT/US2013/078238, mailed on Apr. 25, 2014, pp. 1-10.

Seedorf et al., The genome of Clostridium kluyyeri, a strict anaerobe with unique metabolic figures, PNAS (2008) 105:2128-2133.

Cotter & Chinn, Ethanol and acetate production by clostridium ljungdahlii and clostridium autoethanogenum using resting cells, Bioprocess Biosyst Eng (2009) 32: 36-380.

Kopke et al., Clostridium ljungdahlii represents a microbial production platform based on syngas, PNAS (2010) 107:13087-13092.

\* cited by examiner

METHOD FOR PRODUCTION OF N-BUTANOL FROM SYNGAS USING SYNTROPHIC CO-CULTURES OF ANAEROBIC MICROORGANISMS

FIELD OF THE INVENTION

The invention provides methods and systems for production of n-butanol and other C4-containing products from syngas using syntrophic co-cultures of anaerobic microorganisms.

BACKGROUND OF THE INVENTION

Butanol is an important industrial chemical with a wide range of applications. It can be used as a motor fuel particularly in combination with gasoline to which it can be added in all proportions. Isobutanol can also be used a precursor to Methyl Tertiary Butyl Ether (MTBE). Currently the world production of n-Butanol is 3.5 million tons/yr (7.7 billion lb/yr). Furthermore, conversion of alcohols to long chain linear hydrocarbons that would be suitable for jet fuel use are being developed and demonstrated, which could further increase the demand for n-Butanol (The Naval Air Warfare Center—Weapons Division, (2012) Cobalt and Abermarle). For many centuries, simple sugars have been fermented into butanol with the help of *Saccharomyces cerevisae*. Fermentation of carbohydrates to acetone, butanol and ethanol (ABE) is well known and was commercially practiced worldwide from around 1915 to 1955 (Beesch, S. C. (1953) A Microbiological process Report—Applied Microbiology, 1, 85-95). With the advent of petrochemical processes and low cost petrochemical feedstocks the carbohydrate based processes became unattractive and were discontinued.

Further development and modernization of the ABE process was undertaken by several organizations. In the mid-1980s the Corn Products Corporation developed asporogenic strains and a multi-staged fermentation process that considerably improved the process economics (Marlatt, J. A. and R. Datta, (1986) Acetone-Butanol Fermentation Process, Biotechnology Progress (1986) 2, 1.23-28). Currently, two companies, Gevo and Butamax are engaged in conversion of several ethanol plants using recombinant microorganisms to produce iso-butanol for new chemical uses. See U.S. Pat. No. 8,017,375 and U.S. Pat. No. 7,851,188. In all of these developments the primary feedstock is carbohydrate, primarily starch from corn.

The limitations for carbohydrate feedstocks are well known and some are fundamental. Starch and sugars from agricultural crops run into competing issues of food vs. energy/chemical production as well as the cost of the feedstocks and their availability. For lignocellulosic feedstocks such as woody biomass, grasses etc. the cost and yield from pretreatment and hydrolysis processes are very limiting. For example, typical woody biomass contains 50% cellulose while the remainder consists of hemicelluloses, lignin and other fractions. The chemical energy content of the fermentable fractions is often less than 50% of that of the feedstock, putting fundamental limitations on product yield.

Attempts have been made to improve the alcohol yield of bacterium that ferment a variety of sugars to acetate and butyrate. The art has sought to employ recombinant techniques to transform bacterium such as *C. acetobutylicum* (Green et al. (1996) Genetic manipulation of acid formation pathways, Green et al. Microbiology), 142, 2079-2086) and *C. tyrobutyricum* (X. Liu et al. (2006) Construction and Characterization of ack Deleted Mutant of *Clostridium tyrobutyricum*, Biotechnology Pref., 22, 1265-1275). However, such techniques have only resulted in transformation occurring at low frequencies.

Several microorganisms are able to use one-carbon compounds as carbon source and some even as an energy source. Synthesis gas is a common substrate for supplying the one carbon compounds such as CO and $CO_2$ and as well as hydrogen. Synthesis gas can be produced by gasification of the whole biomass source without the need to unlock certain fractions. Synthesis gas can also be produced from other feedstocks via gasification of: (i) coal, (ii) municipal waste (iii) plastic waste, (iv) petcoke and (v) liquid residues from refineries or from the paper industry (black liquor). Synthesis gas can also be produced from natural gas via steam reforming or autothermal reforming (partial oxidation).

When the syngas source is biomass, gasification technology converts all the components of the feedstock primarily to a mixture of CO, $H_2$, $CO_2$ and some residual $CH_4$, typically with 75 to 80% cold gas efficiency i.e. 75 to 80% of the chemical energy of the feedstock is available for further chemical or biological conversion to target products. The rest of the energy is available as heat that can be used to generate steam to provide some or all of the process energy required. Furthermore, a wide range of feedstocks, both renewable such as woody biomass, agricultural residues, municipal wastes etc. or non-renewable such as natural gas, can be gasified to produce these primary components. Natural gas can be economically reformed to syngas with a wide variety of technologies using steam, oxygen, air or combinations thereof. This syngas has very good cold gas efficiency of approximately 85% to produce CO, $H_2$ and $CO_2$ with a wide range of target compositions.

Hence, syngas is a very economical feedstock that can be derived from a wide range of raw materials both renewable and non-renewable. Thus conversion of syngas to butanol with high yield and concentrations would lead to economical production of this important chemical.

The ability of anaerobic bacteria to produce n-butanol from the primary syngas components CO and $H_2/CO_2$ was discovered and reported in 1990/1991 by a team from the Michigan Biotechnology Institute, (A. Grethlein et al. (1991) Evidence of n-Butanol Production from Carbon Monoxide, Journal of Fermentation and Bioengineering, 72, 1, 58-60); (Grethlien et al. (1990) Continuous Production of Mixed Alcohols and Acids from Carbon Monoxide, Journal of Fermentation and Bioengineering, 24-25(1):875-885). Later, other organizations such as University of Oklahoma and Oklahoma State University also isolated new organisms namely *Clostridium Carboxydivorans* that also showed such conversion and n-butanol production (J. S. Liou et al. (2005) *Clostridium Carboxidivorans* sp. nov. a solvent producing *clostridium* Internation Journal of Systematic and Evolutionary Microbiology 55(5):2085-2091). Subsequent fermentation development with these and other organisms in single culture fermentations have not been very successful— the n-butanol concentrations were achieved in the range of approximately 3 g/liter and the yield ranged from 20 to 45% of theoretical (% electrons to product) (see previous three references and Guilaume Bruant et al. (2010) Genomic Analysis of Carbon Monoxide Utilization and Butanol Production by *Clostridium carboxidivorans*, PLoS One, 5(9)). For a commercially successful process, the n-butanol concentration should be in the range of 8-10 g/liter and the yield should be in the 80% range, otherwise processing and separations costs become unattractive.

To overcome these barriers multi-stage fermentations with two or more organisms such as *Butyribacterium methylotrophicum* and *Clostridium acetobutylicum* have been proposed (Worden et al. (1991) Production of butanol and ethanol from synthesis gas via fermentation, Fuel, 70, 6154-619). The former would produce butyric acid and butanol at low concentrations from syngas and the latter would uptake these while converting carbohydrates to produce more butanol. Since *C. acetobutylicum* strains are able to produce 15 g/liter butanol the separations process would be viable. Such a combination could provide some increases in yield and product recovery, but it would be very cumbersome requiring two different types of feedstocks, syngas and carbohydrates as well as separate bioreactors one for gas conversion and another for carbohydrate conversion. Furthermore, in this scheme the carbohydrate feeding the *Clostridium acetobutylicum* is the primary feedstock and not the more economical syngas fed to the *Butyribacterium methylotrophicum* and all the limitations of carbohydrate feedstocks described above will be prevalent.

A more efficient conversion of syngas takes place when converting it to ethanol and acetate. The biochemical pathway of such synthesis gas conversion is described by the Wood-Ljungdahl Pathway. Fermentation of syngas to ethanol and acetate offers several advantages such as high specificity of the biocatalysts, lower energy costs (because of low pressure and low temperature bioconversion conditions), greater resistance to biocatalyst poisoning and nearly no constraint for a preset $H_2$ to CO ratio (M. Bredwell et al. (1999) Reactor design issues for synthesis-gas fermentations, Biotechnology Progress 15, 834-844); (Klasson et al. (1992), Biological conversion of synthesis gas into fuels", International Journal of Hydrogen Energy 17, p. 281). Acetogens are a group of anaerobic bacteria able to convert syngas components, like CO, $CO_2$ and $H_2$ to acetate and ethanol the reductive acetyl-CoA or the Wood-Ljungdahl pathway.

Several anaerobic bacteria have been isolated that have the ability to ferment syngas to ethanol, acetic acid and other useful end products. *Clostridium ljungdahlii* and *Clostridium autoethanogenum*, were two of the first known organisms to convert CO, $CO_2$ and $H_2$ to ethanol and acetic acid. Commonly known as homoacetogens, these microorganisms have the ability to reduce $CO_2$ to acetate in order to produce required energy and to produce cell mass. The overall stoichiometry for the synthesis of ethanol using three different combinations of syngas components is as follows (J. Vega et al. (1989) The Biological Production of Ethanol from Synthesis Gas, Applied Biochemistry and Biotechnology, 20-1, p. 781):

$$6CO+3H_2O \rightarrow CH_3CH_2OH+4CO_2$$

$$2CO_2+6H_2 \rightarrow CH_3CH_2OH+3H_2O$$

$$6CO+6H_2 \rightarrow 2CH_3CH_2OH+2CO_2$$

The primary product produced by the fermentation of CO and/or $H_2$ and $CO_2$ by homoacetogens is ethanol principally according to the first two of the previously given reactions. Homoacetogens may also produce acetate. Acetate production occurs via the following reactions:

$$4CO+2H_2O \rightarrow CH_3COOH+2CO_2$$

$$4H_2+2CO_2 \rightarrow CH_3COOH+2H_2O$$

*Clostridium ljungdahlii*, one of the first autotrophic microorganisms known to ferment synthesis gas to ethanol was isolated in 1987, as an homoacetogen it favors the production of acetate during its active growth phase (acetogenesis)) while ethanol is produced primarily as a non-growth-related product (solventogenesis) (K. Klasson et al. (1992) Biological conversion of synthesis gas into fuels, International Journal of Hydrogen Energy 17, p. 281).

*Clostridium autoethanogenum* is a strictly anaerobic, gram-positive, spore-forming, rod-like, motile bacterium which metabolizes CO to form ethanol, acetate and $CO_2$ as end products, beside it ability to use $CO_2$ and $H_2$, pyruvate, xylose, arabinose, fructose, rhamnose and L-glutamate as substrates (J. Abrini, H. Naveau, E. Nyns), "*Clostridium autoethanogenum*, Sp-Nov, an Anaerobic Bacterium That Produces Ethanol from Carbon-Monoxide", Archives of Microbiology, 161(4), p. 345, 1994).

Anaerobic acetogenic microorganisms offer a viable route to convert waste gases, such as syngas, to useful products, such as ethanol, via a fermentation process. Such bacteria catalyze the conversion of $H_2$ and $CO_2$ and/or CO to acids and/or alcohols with higher specificity, higher yields and lower energy costs than can be attained by traditional production processes. While many of the anaerobic microorganisms utilized in the fermentation of ethanol also produce butanol as a secondary product, to date, no single anaerobic microorganism has been described that can utilize the syngas fermentation process to produce high yields of butanol.

Therefore a need in the art remains for methods using microorganisms in the production of butanol using syngas as the primary fermentation substrate.

SUMMARY OF THE INVENTION

Provided herein are methods for producing butanol comprising exposing gaseous substrates selected from the group consisting of carbon monoxide, carbon dioxide and hydrogen or combinations thereof to a syntrophic co-culture comprising a C1-fixing homacetogenic microorganism having the Wood Ljungdahl pathway and a C4-butyrate producing microorganism having at least one of the BuCoAAT pathway and the BuK pathway under conditions effective for the syntrophic co-culture to convert the gaseous substrate into butanol and/or into butyric acid.

In particular embodiments of the invention the gaseous substrate comprises CO and $H_2$. In other embodiments of the invention the gaseous substrate is syngas produced by the reforming of natural gas into CO, $CO_2$, $H_2$ and $CH_4$.

In particular embodiments of the invention the syntrophic co-culture produces butyric acid and the C1-fixing homoacetogenic microorganism converts the butyric acid into butanol, In other particular embodiments the syntrophic co-culture produces at least 2 grams/liter of butanol. In yet other particular embodiments the syntrophic co-culture produces n-butanol.

In particular embodiments of the invention the C1-fixing homoacetogenic microorganism is selected from the group consisting of *Clostridium coskatii*, *Clostridium ljungdahlii*, *Clostridium authoethanogenium*, and *Clostridium ragsdalei*.

In other particular embodiments of the invention the C4-butyrate producing microorganism is selected from the group consisting of *Clostridium kluyveri*, *Clostridium carboxidivorans*, and *Butyribacterium methylotrophicum*. In yet other embodiments of the invention the C4-butyrate producing microorganism uses the BuCoAAT pathway and/or BuK pathway for the production of butyrate.

In particular embodiments of the invention the syntrophic co-culture is formed by first growing a first culture of one or more of the C1-fixing homoacetogenic microorganism under suitable fermentation conditions to produce ethanol and acetate at concentration of at least 1 g/l and then inoculating the first culture with a second culture of the C4-butyrate producing microorganism to produce the syntropic co-coculture. In some embodiments of the invention the syntrophic co-culture can be formed in a planktonic bioreactor and can be further transferred from a planktonic reactor to a membrane supported bioreactor.

In particular embodiments of the invention the pH of the syntrophic co-culture is maintained between about 5.0 to 7.0.

In other aspects of the invention an anaerobic syntrophic system for conversion of syngas to butanol is provided. The system comprises syngas, culture media, a C1-fixing homoacetogenic microorganism having the Wood Ljungdalii pathway and a C4-producing butyrate microorganism having at least one of the BuCOAT pathway and the BuK pathway.

In particular embodiments of the invention the C1-fixing homoacetogenic microorganism of the anaerobic system is selected from the group consisting of *Clostridium coskatii*, *Clostridium ljungdahlii*, *Clostridium authoethanogenium*, and *Clostridium ragsdalei*.

In other particular embodiments of the invention the C4-butyrate producing microorganism of the anaerobic syntrophic system is selected from the group consisting of *Clostridium kluyveri*, *Clostridium caroxidivorans* and *Butyribacterium methylotrophicum*. In yet other particular embodiments the system contains one or more C4-butyrate producing microorganisms having the BuCOAT pathway and the BuK pathway.

In still other particular embodiments of the invention the pH of the culture media of the anaerobic syntrophic system is maintained between about 5.0 to about 7.0.

Specific preferred embodiments of the invention will become evident from the following more detailed description of certain preferred embodiments and the claims.

BRIEF DESCRIPTION OF THE DRAWINGS

These and other objects, features, and embodiments of the invention will be better understood from the following detailed description taken in conjunction with the drawings, wherein.

DETAILED DESCRIPTION OF THE INVENTION

The invention provides methods for the production of butanol and other C4-containing products from syngas by syntrophic co-cultures of anaerobic microorganisms. In other aspects, the invention provides anaerobic systems for conversion of syngas to butanol.

As used herein, synthesis gas (syngas) is a gas containing carbon monoxide, carbon dioxide and frequently hydrogen. "Syngas" includes streams that contain carbon dioxide in combination with hydrogen and that may include little or no carbon monoxide. "Syngas" may also include carbon monoxide gas streams that may have little or no hydrogen.

As used herein, the term "syntrophic" refers to the association of two or more different types (e.g. organisms, populations, strains, species, genera, families, etc.) of anaerobic microorganisms which are capable of forming a tightly associated metabolic relationship.

As used herein, the term "co-culture" of microorganisms refers to joint incubation or incubation together, of the syntrophic microorganisms. In the context of the present invention, the co-culture does not require cellular population growth during the joint incubation of the syntrophic microorganisms.

Figure 1:
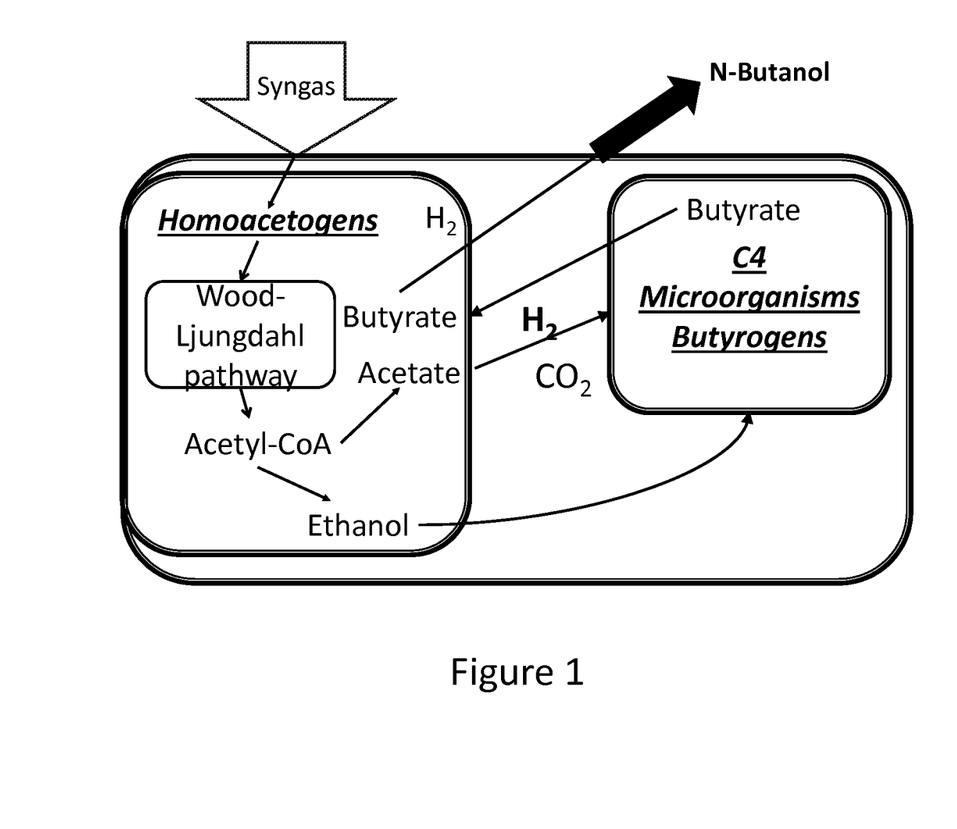
FIG. 1 is a diagram of a schematic conversion path showing the production of n-butanol from a substrate input of syngas.

In one embodiment of the invention illustrated in FIG. 1, two types of anaerobic microorganism are utilized to create the syntrophic co-cultures for production of butyrate. The first type of microorganism in the syntrophic co-culture is a primary C1-fixing homacetogenic microorganism, which utilizes syngas as the sole carbon and electron source and produces C1 compounds such as ethanol and acetate as the dissimilatory metabolite products. The second type of microorganism in the syntrophic co-culture is capable of growing on the dissimilatory metabolites of the C1-fixing homacetogenic microorganism (ethanol and acetate) as its sole carbon and/or electron source to produce a C4-carbon molecule, such as butanol or butyric acid, as its primary product or together with syngas (as additional carbon and/or electron source) convert the metabolites of the C1-carbon fixing microorganism to C4-carbon molecules. This second microorganism shall be referred to herein as the C4-butyrate producing microorganism. Advantageously, the C1-fixing homacetogenic microorganism may also be capable of converting the butyrate produced by the C4-producing microorganism into butanol and more often n-butanol. The term "butanol" refers to all four isomers of C4 alcohol (e.g. 2-butanol, isobutanol, 1-butanol and tert-butanol) and the term "n-butanol" refers to 1-butanol.

The C1-fixing microorganisms of the invention are also homoacetogens. Homoacetogens have the ability, under anaerobic conditions, to produce acetic acid and ethanol from the substrates, $CO+H_2O$, or $H_2+CO_2$ or $CO+H_2+CO_2$. The CO or $CO_2$ provide the carbon source and the $H_2$ or CO provide the electron source for the reactions producing acetic acid and ethanol. C1-fixing microorganisms suitable for use in the inventive method include, without limitation, homoacetogens such as *Clostridium ljungdahlii*, *Clostridium autoethanogenum*, *Clostridium ragsdalei*, and *Clostridium coskatii*. Additional C1 fixing microorganisms that are suitable for the invention include *Alkalibaculum bacchi*, *Clostridium thermoaceticum*, and *Clostridium aceticum*.

Figure 2:
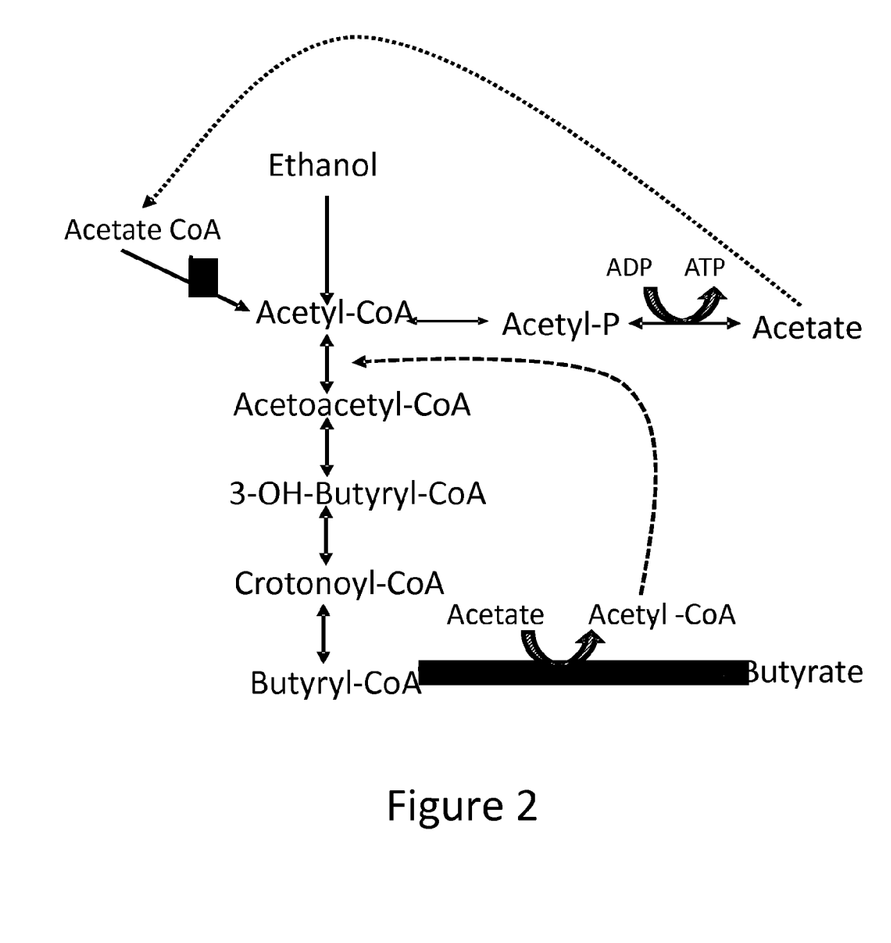
FIG. 2 is a detailed diagram of acetate and ethanol conversion by a butyrogen to produce butyrate using the Butyrl CoA Acetyl Transferase Pathway.

In particular embodiments, the syntrophic C4-producing microorganism is a butyrogen capable of growing on ethanol and/or acetate as its primary carbon source. Butyrogens as referred to hereafter, are any microorganism capable of converting syngas intermediates, such as ethanol and acetate and some hydrogen to primarily n-butyrate. Butyrogens of the invention utilize at least one of two distinct pathways for butyrate production—the Butyrl CoA Acetyl Transferase pathway (shown in FIGS. 2 and 3) and the Butyrl Kinase (BuK) pathway (shown in FIG. 3). As can be seen from the FIG. 2, the Butyryl CoA Acetyl Transferase (BuCoAAT) pathway converts ethanol and acetate to butyrate:

$$Ethanol + Acetate \leftrightarrow Butyrate + H_2O$$

Figure 3:
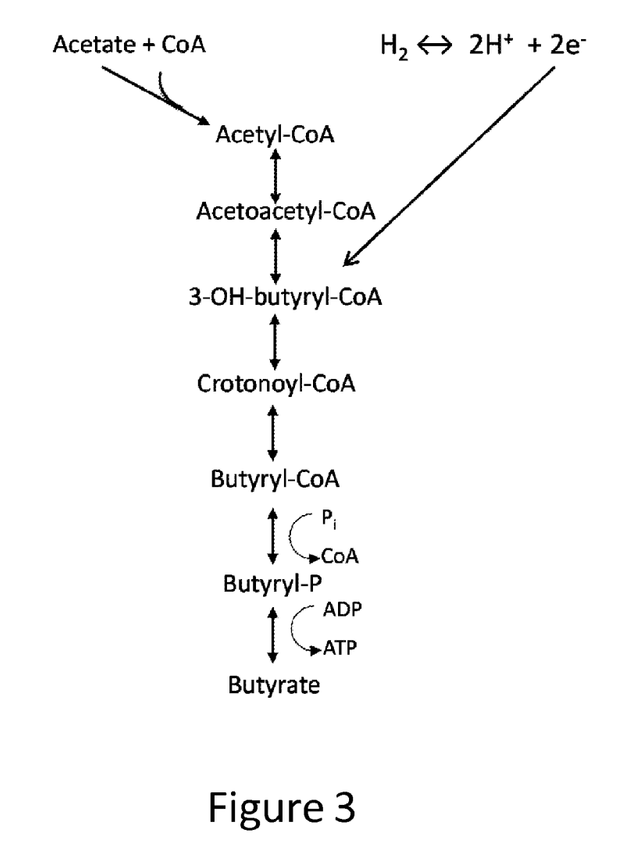
FIG. 3 is a detailed diagram of acetate conversion by a butyrogen to produce butyrate using the Butyrl Kinase Pathway.

As shown in FIG. 3 the BuK pathway converts acetate and hydrogen to Butyrate.

$$2H_2 + 2Acetate \leftrightarrow Butyrate + 2H_2O$$

In the BuCOAAT pathway ethanol and acetate are converted to butyrate through a Butyrl CoA intermediate. Similarly acetate plus reducing equivalents through $H_2$ oxidation are converted to butyrate through a butyrl CoA intermediate. The pathways differ in their conversion steps from butyryl CoA to butyrate. The BuCoAAT pathway converts butyrl CoA to butyrate through the BuCoAAT enzyme while the BuK pathway converts butyryl CoA through a BuK enzyme.

Suitable butyrogens for this invention include any microorganisms that contain either or both of the BuCoAAT pathway and BuK pathway and can grow on acetate and ethanol or on acetate and hydrogen as typically found in syngas.

While many microorganisms are known to produce butyrate from various carbohydrate sources (*C. butyricum, C. acetobutylicum, C. tyrobutyricum, C. beijerinckii, C. pasteurianum, C. barkeri, C. thermobutyricum, C. thermopalmarium, Butyrvibrio, Sarcina, Eubacterium, Fusobacterium*, and *Megasphera*), only a few are known to grow exclusively on ethanol, acetate or syngas such as *Clostridium kluyveri, Clostridium carboxidivorans*, and *Butyribacterium methylotrophicum*

The homoacetogens of the invention have the primary Wood Ljungdahl pathway to convert the CO and $H_2/CO_2$ from the syngas feed to ethanol and acetate which are then utilized by the butyrogens to produce butyrate. The homoacetogens can uptake the butyrate and very efficiently convert it to n-butanol because of the favored thermodynamics. Such syntrophy can be developed to form very close association so that interspecies proton and electron and species transfer occur very efficiently across very short distances (approximately 1 micron). Such conditions achieve good product concentrations (8-10 g/liter n-butanol) and yields (~80% of electrons to n-butanol) in a single fermenter system. This combination of microorganisms and substrates vastly improves the n-butanol production over that produced by single culture fermentations.

The pairing of the homoacetogens with the butyrogens provided herein demonstrates a vast improvement over the prior art. Table 1 shows a comparison of single culture production to the use of syntrophic cultures. As the results show, a four-fold increase in the concentration of n-butanol was achieved. Thus, in particular embodiments of the invention, high yield production of butanol directly from syngas was achieved which leads to economical and efficient production processes for butanol from a wide range of feedstocks.

TABLE 1

| Bio-conversion method | n-Butanol concentration achieved (g/l) | n-Butanol yield achieved (% of electrons) | Ethanol by product (% of electrons) | Reference |
|---|---|---|---|---|
| *B. methylotrophicum* (single culture) | 2 to 3 | 40 to 45% | 10-20% | See Grethlein et al., Journal of Fermentation and Bioengineering, 72, 1, 58-60(1991). |
| *C. carboxidivorans* (single culture) | 2 to 2.5 | 20 to 25% | 20 to 25% | Liou et al. International Journal of Systematic and Evolutionary Microbiology 55(5): 2085-2091) (2005) Guillaume et al. PLoS One, 5(9)) (2010) |
| Syntrophic Co-culture | 8 to 9 | 60 to 80% | 10 to 25% | Examples 1 and 2 |

A successful syntrophic relationship between the different microorganism cultures of the present invention require that the homoacetogens and the butyrogens are brought into close physical association with each other. In particular embodiments, the C1 converting homoacetogens with the primary Wood Ljungdahl pathway are brought together in an intimately mixed co-culture with the butyrogens. For example, syntrophic co-culture is formed by first growing a single species or a combination of known homoacetogen species on a syngas feed. Growth of the homoacetogens continues until they produce ethanol and acetate, normally at a concentration of at least 1 g/l and more typically in a moderate concentration range of 8 to 15 g/l and a cell concentration producing an optical density (O.D.) of about 2.0. Once the homoacetogens have produced a desired concentration of ethanol and acetate and the fermenter has reached a desired O.D., the homoacetogens are inoculated with one or more selected butyrogen species that are enriched from growth on acetate, ethanol and syngas. By maintaining growth and operating conditions such as pH, dilution rate, key nutrients etc., a stable syntrophic co-culture is developed that forms very close associations between the different microorganisms.

Those skilled in the art will be aware of other methods to initiate and grow the co-culture. Such methods may include the use of different substrates to first grow the butyrogen and then inoculate the fermentation medium containing the butyrogen with the homoacetogen. Another method for establishing a syntrophic association capable of converting syngas to butanol involves the growing of two or more defined cultures and establishing the pairing of these separate cultures.

Another method of pairing involves first growing the C4-producing butyrogen in a fermenter using ethanol and acetate as substrates until maximum productivity targets of butyric acid and butanol has been reached. Once the maximum productivity target has been reached a seed culture of the C1-fixing homoacetogen is added directly to the fermenter containing the butyrogen culture. Syngas mass transfer to the fermentation vessel is gradually increased to balance the gas consumption of the C1-fixing homoacetogen. The ethanol or acetate used to grow the butyrogen are gradually decreased to zero as the C1-fixing homoacetogen begins to provide this substrate.

A modification of this last method of establishing a syntrophic culture involves first growing the C4-producing butyrogen culture in a fermenter with a biofilm support material that is either stationary or floating within the reactor. An example of such material is the Mutag Biochips. This method allows the butyrogen microorganism to first establish a biofilm on the carrier material thereby increasing the cell retention time versus the HRT of the fermenter. Again, target butyrogen productivity is reached before seeding the fermenter with the C1-fixing homoacetogen.

Another method to establish a syntrophic culture capable of producing butanol from syngas involves the initial mixing together of two or more cultures, one of which is a C1-fixing homoacetogen capable of growing on syngas and producing ethanol and acetate. The other culture(s) is a C4-producing butyrogen capable of converting ethanol or acetate to butyrate. Ethanol and acetate feed can gradually be decreased to zero as the production of these substrates by the C1-fixing homoacetogens increases to balance the substrate needs of the butyrogen production.

The methods of the present invention can be performed in any of several types of fermentation apparatuses that are known to those of skill in the art, with or without additional modifications, or in other styles of fermentation equipment that are currently under development. Examples include but are not limited to conventional stirred tank fermenters (CSTRS), bubble column bioreactors (BCBR), membrane supported bioreactors (MSBR), two stage bioreactors, trickle bed reactors, membrane reactors, packed bed reactors containing immobilized cells, etc. Bioreactors may also include a column fermenter with immobilized or suspended cells, a continuous flow type reactor, a high pressure reactor, or a suspended cell reactor with cell recycle. Furthermore, reactors may be arranged in a series and/or parallel reactor system which contains any of the above-mentioned reactors. For example, multiple reactors can be useful for growing cells under one set of conditions and generating n-butanol (or other products) with minimal growth under another set of conditions.

Establishing the necessary close association of the co-culture may be influenced by the type of bioreactor employed for practice of the invention. For example in the case of planktonic type bioreactors the syntrophic co-culture may continue in a growth phase and be passaged up to larger fermentation vessels. In the case of an MSBR, an established co-culture from a planktonic fermenter may be used to inoculate the membranes. However, an MSBR may also be inoculated by a series of inoculations that alternate between addition of the homoacetogen and addition of the butyrogen.

These apparatuses will be used to develop and maintain the C1-fixing homoacetogen and butyrogen cultures used to establish the syntrophic metabolic association. The chief requirements of such an apparatus include:

a. Axenicity;
b. Anaerobic conditions;
c. Suitable conditions for maintenance of temperature, pressure, and pH;
d. Sufficient quantities of substrates are supplied to the culture;
e. Optimum mass transfer performance to supply the gases to the fermentation medium
e. The end products of the fermentation can be readily recovered from the bacterial broth.

Suitable gas sources of carbon and electrons are preferably added during the inoculation. In addition to those already described these gaseous sources come from a wide range of materials and include "waste" gases such as syngas, oil refinery waste gases, steel manufacturing waste gases, gases produced by steam, autothermal or combined reforming of natural gas or naphtha, biogas and products of biomass, coal or refinery residues gasification or mixtures of the latter. Sources also include gases (containing some $H_2$) which are produced by yeast, clostridial fermentations, and gasified cellulosic materials. Such gaseous substrates may be produced as byproducts of other processes or may be produced specifically for use in the methods of the present invention. Those of skill in the art will recognize that any source of substrate gas may be used in the practice of the present invention, so long as it is possible to provide the microorganisms of the co-culture with sufficient quantities of the substrate gases under conditions suitable for the bacterium to carry out the fermentation reactions.

In one embodiment of the invention, the source of CO, $CO_2$ and $H_2$ is syngas. Syngas for use as a substrate may be obtained, for example, as a gaseous product of coal or refinery residues gasification.

In addition to those sources as described, syngas can be produced by gasification of readily available low-cost agricultural raw materials expressly for the purpose of bacterial fermentation, thereby providing a route for indirect fermentation of biomass to alcohol. There are numerous examples of raw materials which can be converted to syngas, as most types of vegetation could be used for this purpose. Suitable raw materials include, but are not limited to, perennial grasses such as switchgrass, crop residues such as corn stover, processing wastes such as sawdust, byproducts from sugar cane harvesting (bagasse) or palm oil production, etc. Those of skill in the art are familiar with the generation of syngas from such starting materials. In general, syngas is generated in a gasifier from dried biomass primarily by pyrolysis, partial oxidation, and steam reforming, the primary products being CO, $H_2$ and $CO_2$. The terms "gasification" and "pyrolysis" refer to similar processes; both processes limit the amount of oxygen to which the biomass is exposed. The term "gasification" is sometimes used to include both gasification and pyrolysis.

Combinations of sources for substrate gases fed into the fermentation process may also be utilized to alter the concentration of components in the feed stream to the bioreactor. For example, the primary source of CO, $CO_2$ and $H_2$ may be syngas, which typically exhibits a concentration ratio of 37% CO, 35% $H_2$, and 18% $CO_2$, but the syngas may be supplemented with gas from other sources to enrich the level of CO (i.e., steel mill waste gas is enriched in CO) or $H_2$.

The syntrophic co-cultures of the present invention must be cultured and used under anaerobic conditions. As used herein, "anaerobic conditions" means the level of oxygen ($O_2$) is below 0.5 parts per million in the gas phase of the environment to which the microorganisms are exposed. One of skill in the art will be familiar with the standard anaerobic techniques for culturing these microorganisms (Balch and Wolfe (1976) Appl. Environ. Microbiol. 32:781-791; Balch et al., 1979, Microbiol. Rev. 43:260-296), which are incorporated herein by reference. Other operating conditions for the established co-culture will usually include a pH in a range of 5 to 7.

A suitable medium composition used to grow and maintain syntrophic co-cultures or separately grown cultures used for sequential fermentations, includes a defined media formulation. The standard growth medium is made from stock solutions which result in the following final composition per Liter of medium. The amounts given are in grams unless stated otherwise. Minerals: NaCl, 2; $NH_4Cl$, 25; KCl, 2.5; $KH_2PO_4$, 2.5; $MgSO_4.7H_2O$, 0.5; $CaCl_2.2H_2O$, 0.1. Trace metals: $MnSO_4.H_2O$, 0.01; $Fe(NH_4)_2(SO_4)_2.6H_2O$, 0.008; $CoCl_2.6H_2O$, 0.002; $ZnSO_4.7H_2O$, 0.01; $NiCl_2.6H_2O$, 0.002; $Na_2MoO_4.2H_2O$, 0.0002; $Na_2SeO_4$, 0.001; $Na_2WO_4$, 0.002. Vitamins (amount, mg): Pyridoxine HCl, 0.10; thiamine HCl, 0.05, riboflavin, 0.05; calcium pantothenate, 0.05; thioctic acid, 0.05; p-aminobenzoic acid, 0.05; nicotinic acid, 0.05; vitamin B12, 0.05; mercaptoethane sulfonic acid, 0.05; biotin, 0.02; folic acid, 0.02. A reducing agent mixture is added to the medium at a final concentration of 0.1 g/L of cysteine (free base); and 0.1 $Na_2S.2H_2O$. Medium compositions can also be provided by yeast extract or corn steep liquor or supplemented with such liquids.

In general, fermentation of the syntrophic co-culture will be allowed to proceed until a desired level of butanol is produced in the culture media. Preferably, the level of butanol produced is in the range of 2 grams/liter to 75 grams/liter and most preferably in the range of 6 grams/liter to 15 grams/liter. Alternatively, production may be halted when a certain rate of production is achieved, e.g. when the rate of production of a desired product has declined due to, for example, build-up of bacterial waste products, reduction in substrate availability, feedback inhibition by products, reduction in the number of viable bacteria, or for any of several other reasons known to those of skill in the art. In addition, continuous culture techniques exist which allow the continual replenishment of fresh culture medium with concurrent removal of used medium, including any liquid products therein (i.e. the chemostat mode). Also techniques of cell recycle may be employed to control the cell density and hence the volumetric productivity of the fermenter.

The products that are produced by the microorganisms of this invention can be removed from the culture and purified by any of several methods that are known to those of skill in the art. For example, butanol can be removed by distillation at atmospheric pressure or under vacuum, by adsorption or by other membrane based separations processes such as pervaporation, vapor permeation and the like.

This invention is more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The terms used in the specification generally have their ordinary meanings in the art, within the context of the invention, and in the specific context where each term is used. Some terms have been more specifically defined to provide additional guidance to the practitioner regarding the description of the invention.

EXAMPLES

The Examples which follow are illustrative of specific embodiments of the invention, and various uses thereof. They are set forth for explanatory purposes only, and are not to be taken as limiting the invention.

Example 1

Establishment of Stable Syntrophic Pairing of Homoacetogen with Butyrogens

Figure 4:
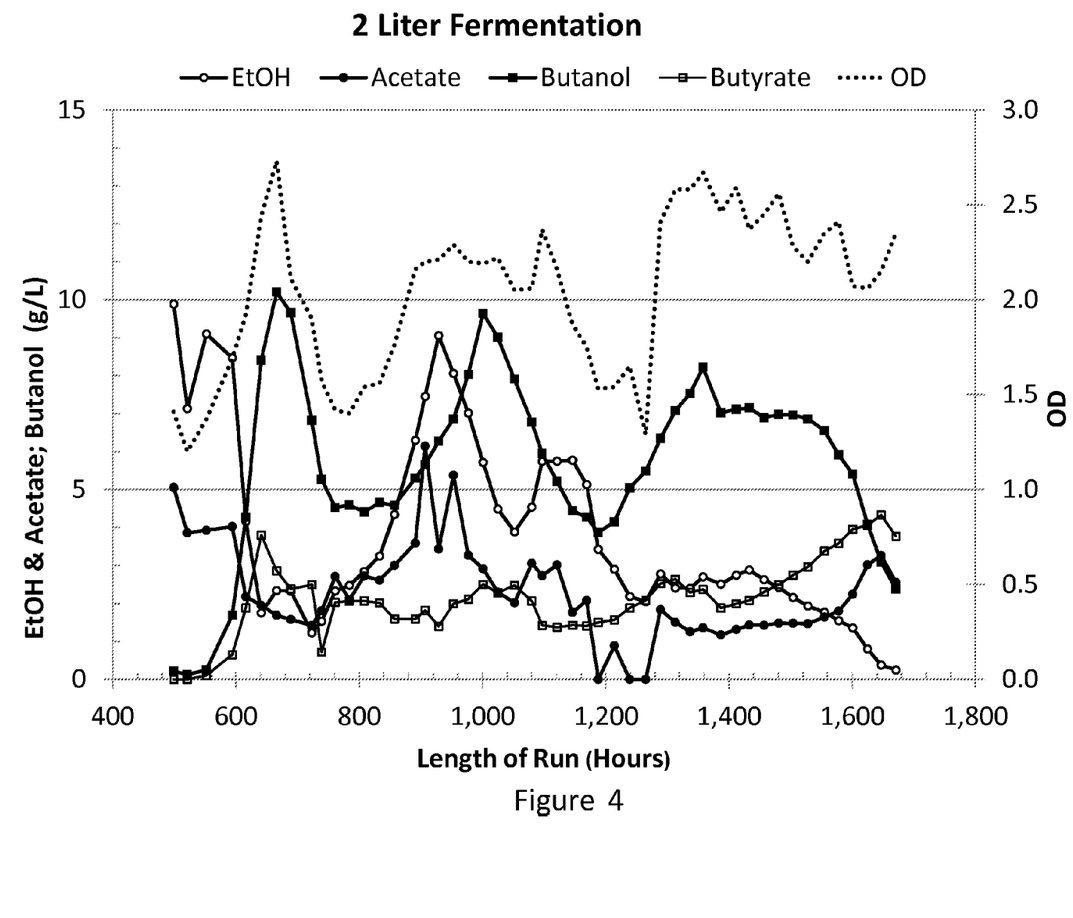
FIG. 4 is a time plot of the butanol, acetate and ethanol production from a 2 liter fermentation run.

A 2-liter fermentation experiment was run in order to establish a syntrophic pairing of a type strain homoacetogen, *Clostridium autoethanogenum*, and a mixed culture of butyrogens. The mixed culture of *Clostridium autoethanogenum* was first grown to an O.D. of 1.7 on minimal media and syngas with a composition of $H_2$—56%, CO—22%, $CO_2$—5%, and $CH_4$—17% (mol %), 60 mL/min gas flow rate and agitation between 500-600 rpm. The ethanol and acetate concentrations were at 10 and 5 g/L respectively prior to the addition of 200 mL of the mixed butyrogen culture. FIG. 4 shows the concentration of the ethanol, acetate and butanol in the fermenter at the time the mixed butyrogen culture was added. The butyrate and butanol concentrations slowly increased and 6 days after inoculation with the butyrogens, butanol and butyrate concentrations of 8.4 and 3.8 g/L, respectively were achieved. The increase in butanol and butyrate coincided with a decrease in ethanol and acetate to concentrations of 1.8 and 2.0, respectively. During this time period, more than 70% of the electrons consumed as syngas were being converted to butanol and butyrate.

Example 2

Example of Butanol Production in Single Stage Pilot Scale BCBR

Figure 5:
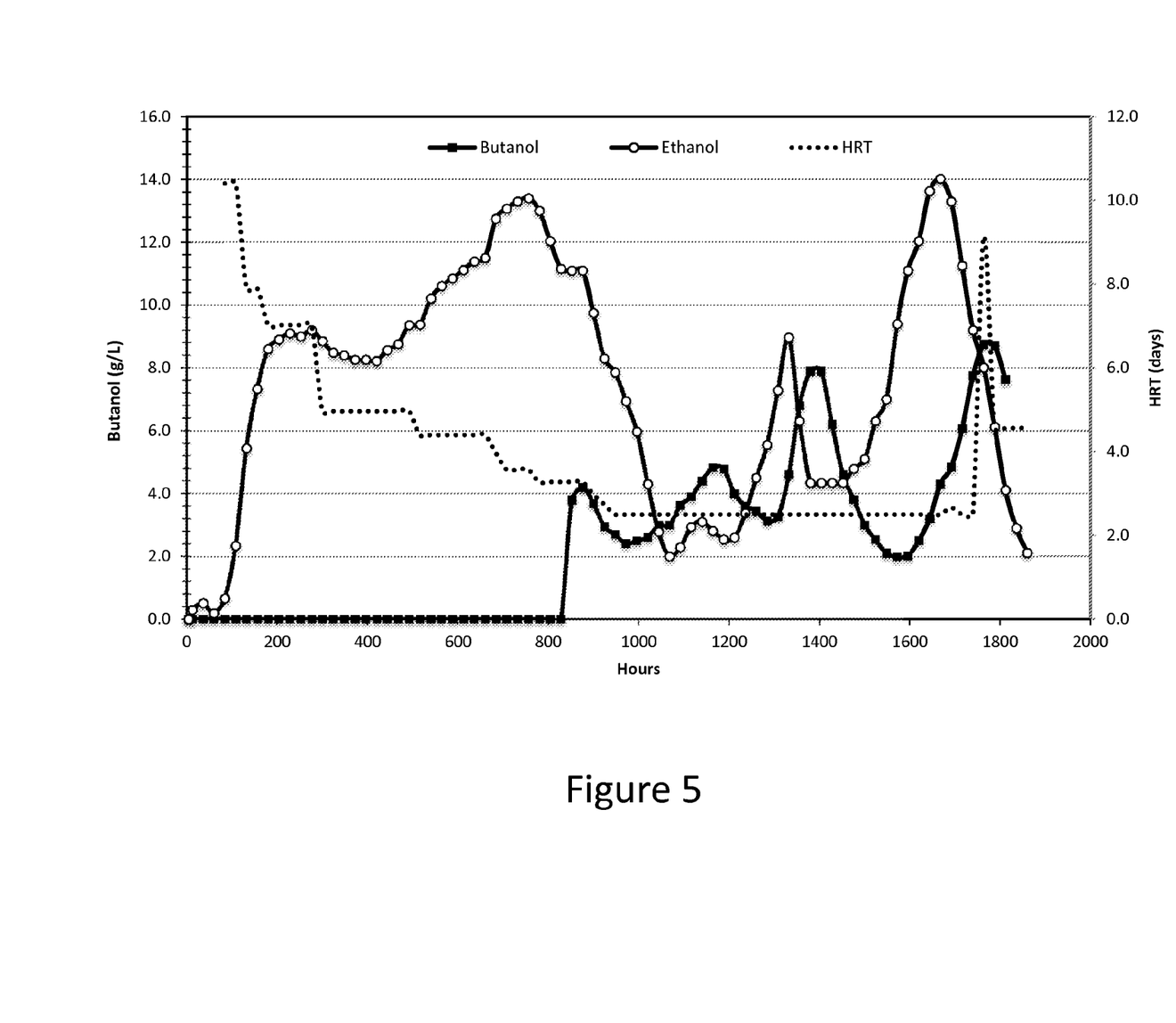
FIG. 5 is a time plot of butanol and ethanol production and hydraulic retention time (HRT) from a 38,000 liter fermentor.

A 38,000 liter pilot scale Bubble Column BioReactor (BCBR) was first brought up to solventogenic conditions producing over 12 g/L of ethanol. The reactor was fed syngas as the only carbon and electron source to support the growth of the homoacetogen, *Clostridium autoethanogenum*. Composition of the syngas was on average, $H_2$—39, CO—29, $CO_2$—17, and $CH_4$—15 (mol %) and the rate of syngas addition varied from 35 to 144 lb/hr at a total fermenter volume of 26,000 liters. The HRT of the fermentation vessel was slowly stepped down from 8 days at the start of the fermentation to 3.3 days by 800 hours. FIG. 5 is a time plot of butanol and ethanol production and hydraulic retention time (HRT) from the 38,000 liter fermentor. After 800 hours, the ethanol producing fermentation was inoculated with a butyrogen culture. After the addition of the butyrogen culture and a further reduction of the HRT, an increase in the concentration of butanol was shown (FIG. 5). Once initial butanol production was observed the HRT was further dropped to 2.5 days. Butanol concentrations rose and remained above 4 g/L and progressively rose as high as 8 g/L for the next 1000 hours under these conditions. Increasing the HRT to 9 days further increased the butanol concentration to 9 g/L total. The butanol concentration was the highest when the fermentation was at 2.5 days HRT Electron flow from syngas consumption to fermentation products during this 1000 hour period show that 60-80% of the electrons ended up as butanol product.

The invention claimed is:
1. A method for producing butanol comprising exposing gaseous substrates comprising carbon source and an electron source to a syntrophic co-culture comprising: a first non-recombinant microorganism that is a C1-fixing homoacetogenic microorganism having the enzymes of the Wood

Ljungdahl pathway; and a second non-recombinant microorganism that is a C4-producing butyrate microorganism having the enzymes of at least one of the Butyryl CoA Acetyl Transferase (BuCoAAT) pathway and the Butyryl Kinase (BuK) pathway under anaerobic conditions effective for the syntrophic co-culture to convert the gaseous substrate into butanol, wherein the carbon source is at least one of carbon monoxide and carbon dioxide and the electron source is at least one of hydrogen and carbon monoxide and wherein the C1-fixing homoacetogenic microorganism is capable of converting the carbon source and the electron source into at least one of ethanol and acetate and wherein the C4-producing butyrate microorganism is a butyrogen capable of converting the ethanol and acetate into n-butyrate.

2. The method of claim 1 wherein the syntrophic co-culture further produces butyric acid and the C1-fixing homoacetogenic microorganism converts the butyric acid into butanol.

3. The method of claim 2 wherein the syntrophic co-culture further produces n-butanol.

4. The method of claim 1 wherein the C1-fixing homoacetogenic microorganism is selected from the group consisting of *Clostridium coskatii, Clostridium ljundahlii, Clostridium autoethanogenum*, and *Clostridium ragsdalei*.

5. The method of claim 1 wherein the butyrogen microorganism uses at least one of the enzymes of the Butyryl CoA Acetyl Transferase (BuCoAAT) pathway and Butyryl Kinase (BuK) pathway for the production of butyrate.

6. The method of claim 1 wherein the butyrogen microorganism is selected from the group consisting of *Clostridium kluyveri, Clostridium carboxidivorans*, and *Butyribacterium methylotrophicum*.

7. The method of claim 1 wherein the syntrophic co-culture is formed by first growing a first culture of one or more of the C1-fixing homoacetogenic microorganism under suitable fermentation conditions to produce ethanol and acetate at concentration of at least 1 g/l and then inoculating the first culture with a second culture of the butyrogen microorganism to produce the syntrophic co-culture.

8. The method of claim 7 wherein the syntrophic co-culture is formed in a planktonic bioreactor.

9. The method of claim 8 wherein the syntrophic co-culture is transferred from a planktonic reactor to a membrane supported bioreactor.

10. The method of claim 1 wherein the gaseous substrate is syngas produced by the reforming of natural gas into CO, $CO_2$, $H_2$ and $CH_4$.

11. The method of claim 1 wherein the pH of the syntrophic co-culture is maintained between about 5.0 to 7.0.

12. The method of claim 2 wherein the syntrophic co-culture produces at least 2 grams/liter of butanol.

* * * * *